(12) United States Patent
Bieri et al.

(10) Patent No.: US 12,317,896 B2
(45) Date of Patent: Jun. 3, 2025

(54) METHOD OF CONTROLLING FUNGI

(71) Applicant: SYNGENTA CROP PROTECTION AG, Basel (CH)

(72) Inventors: Stéphane Bieri, Stein (CH); Dianne Irwin, Bracknell (GB); John Richard Gauvin, Echt (NL); Leon Coulier, Echt (NL); Adriana Carvalho De Souza, Echt (NL)

(73) Assignee: SYNGENTA CROP PROTECTION AG, Basel (CH)

( * ) Notice: Subject to any disclaimer, the term of this patent is extended or adjusted under 35 U.S.C. 154(b) by 481 days.

(21) Appl. No.: 17/799,191

(22) PCT Filed: Jan. 26, 2021

(86) PCT No.: PCT/EP2021/051716
§ 371 (c)(1),
(2) Date: Aug. 11, 2022

(87) PCT Pub. No.: WO2021/160419
PCT Pub. Date: Aug. 19, 2021

(65) Prior Publication Data
US 2023/0081771 A1 Mar. 16, 2023

(30) Foreign Application Priority Data
Feb. 11, 2020 (EP) .................................... 20156749

(51) Int. Cl.
| A01N 43/28 | (2006.01) |
| A23B 2/729 | (2025.01) |
| A23B 7/155 | (2006.01) |
| A23B 9/28 | (2006.01) |
| A23C 9/158 | (2006.01) |
| A61K 8/30 | (2006.01) |

(52) U.S. Cl.
CPC ............ *A01N 43/28* (2013.01); *A23B 2/7295* (2025.01); *A23B 7/155* (2013.01); *A23B 9/28* (2013.01); *A23C 9/1585* (2013.01); *A61K 8/30* (2013.01)

(58) Field of Classification Search
CPC ...... A01N 43/28; A23B 2/7295; A23B 7/155; A23B 9/28; A23C 9/1585; A61K 8/30
See application file for complete search history.

(56) References Cited

U.S. PATENT DOCUMENTS

| 6,919,298 B2 | 7/2005 | Silverman et al. |
| 2017/0227545 A1 | 8/2017 | Mitchell et al. |

FOREIGN PATENT DOCUMENTS

| EA | 014916 B1 | 2/2011 |
| EP | 0367474 A1 | 5/1990 |
| EP | 0374753 A2 | 6/1990 |
| EP | 0401979 A2 | 12/1990 |

(Continued)

OTHER PUBLICATIONS

Written Opinion of the International Searching Authority and International Search Report for International Application No. PCT/EP2021/051716, mailed Apr. 29, 2021.

(Continued)

*Primary Examiner* — Trevor Love
(74) *Attorney, Agent, or Firm* — BakerHostetler; Toni-Junell Herbert

(57) ABSTRACT

A method of controlling or preventing infestation of plants by fungi, wherein a fungicidally effective amount of cyclothiazomycin C, is applied to the plants, to parts thereof or the locus thereof.

18 Claims, 2 Drawing Sheets

(56) References Cited

FOREIGN PATENT DOCUMENTS

Figure 1A:
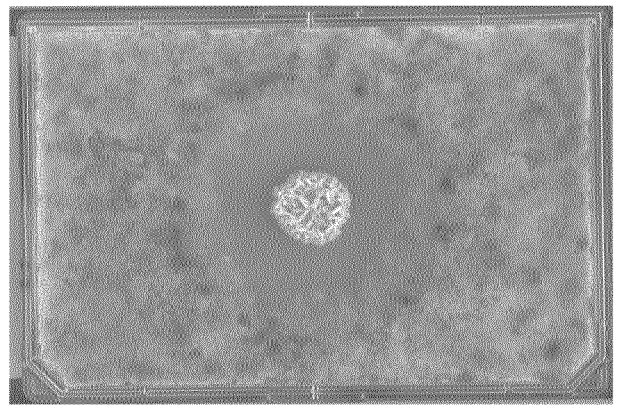

| | | |
|---|---|---|
| EP | 0427529 A1 | 5/1991 |
| EP | 451878 A1 | 10/1991 |
| RU | 2547721 C2 | 4/2015 |
| WO | 9013651 A1 | 11/1990 |
| WO | 9307278 A1 | 4/1993 |
| WO | 9534656 A1 | 12/1995 |
| WO | 9733890 A1 | 9/1997 |
| WO | 03052073 A2 | 6/2003 |
| WO | 2008/052681 A1 | 5/2008 |
| WO | 2011/085084 A1 | 7/2011 |
| WO | 2015191789 A2 | 12/2015 |

OTHER PUBLICATIONS

Mizuhara, Naoko et al., Antifungal thiopeptide cyclothiazomycin B1 exhibits growth inhibition accompanying morphological changes via binding to fungal cell wall chitin, Bioorganic and Medicinal Chemistry, vol. 19, No. 18, Aug. 5, 2011, pp. 5300-5310.

Hashimoto, M et al., An RNA polymerase inhibitor, cyclothiazomycin B1, and its isomer, Bioorganic and Medicinal Chemistry, vol. 14, No. 24, Dec. 15, 2006, pp. 8259-8270.

Extended European Search Report for European Patent Application No. EP 20156749.2, dated Jun. 25, 2020.

METHOD OF CONTROLLING FUNGI

CROSS-REFERENCE TO RELATED APPLICATIONS

This application is a 371 National Stage application of International Application No. PCT/EP2021/051716 filed Jan. 26, 2021, which claims priority to EP 20156749.2, filed Feb. 11, 2020, the entire contents of these applications are hereby incorporated by reference.

The present invention relates to the use of a known compound cyclothiazomycin C to control fungi, particularly in agriculture or horticulture. The invention also relates to fungicidal compositions, particularly agrochemical fungicidal compositions which comprise cyclothiazomycin C, to processes of preparation of the compositions and to uses of cyclothiazomycin C or the compositions for controlling or preventing fungal infestation of substrates, particularly for use in agriculture or horticulture on substrates such as plants, harvested food crops, seeds or non-living materials.

Cyclothiazomycin C is a known compound of formula I,

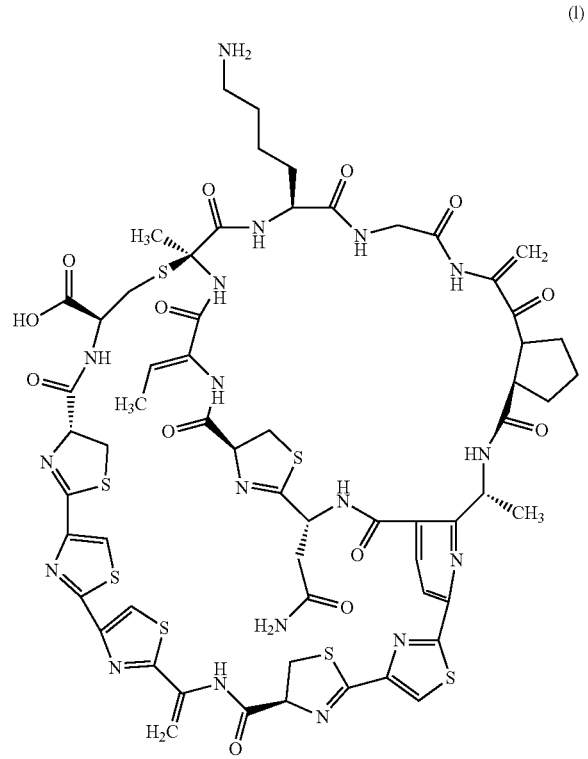 [SMILES: C=C1NC(=O)CNC(=O)[C@H](CCCCN)NC(=O)[C@@]2(C)NC(=O)/C(=C/C)NC(=O)[C@H]3CSC(=N3)[C@@H](CC(N)=O)NC(=O)c3ccc(nc3[C@@H](C)NC(=O)[C@@H]3CCCC3C1=O)-c1nc(cs1)C1=N[C@H](CS1)C(=O)NC(=C)c1nc(cs1)-c1nc(cs1)C1=N[C@@H](CS1)C(=O)N[C@@H](C(=O)O)CS2]

(I)

The structure of cyclothiazomycin C is disclosed on page 3 of WO2015191789. This disclosure also gives examples of the antimicrobial activity of cyclothiazomycin C in Table 6 on page 31. On page 31 after Table 6 it is clearly stated "The greatest inhibitory activity was observed towards the genus *Bacillus*. We decided to also evaluate if cyclothiazomycin C exhibited growth inhibitory action toward a variety of fungal strains, but none was observed."

It has now been found that, surprisingly, Cyclothiazomycin C exhibits useful fungicidal activity against a number of fungal pathogens that commonly infest plants in agriculture and horticulture and can be used as an anti-fungal agent or as a fungicide for various substrates and in various applications.

According to a first aspect of the present invention there is provided a method of controlling or preventing infestation of plants by fungi, wherein a fungicidally effective amount of cyclothiazomycin C is applied to the plants, to parts thereof or the locus thereof.

According to a second aspect of the invention, there is provided an agrochemical composition comprising a fungicidally effective amount of cyclothiazomycin C. Such an agrochemical composition may further comprise an agrochemically-acceptable diluent or carrier.

According to a third aspect of the invention there is provided a method of controlling or preventing infestation of plants by fungi, wherein a fungicidally effective amount of an agrochemical composition comprising cyclothiazomycin C is applied to the plants, to parts thereof or the locus thereof.

According to a fourth aspect of the invention, there is provided the use of cyclothiazomycin C as a fungicide. According to this particular aspect of the invention, the use may exclude methods for the treatment of the human or animal body by surgery or therapy.

Cyclothiazomycin C can be obtained as disclosed in WO2015191789. In particular it is produced by NRRL strain WC-3908 and can be isolated as described in paragraph [0178] of WO2015191789. Strain WC-3908 is publicly available via the ARS Culture Collection (NRRL), 1815N University Street, Peoria, IL, 61604.

Cyclothiazomycin C can be used in the agricultural sector and related fields of use, e.g., as active ingredient for controlling fungal plant pests or on non-living materials for the control of spoilage fungi or fungi potentially harmful to humans. Cyclothiazomycin C has surprising activity at low rates of application and is well tolerated by plants. It has very useful curative and preventive properties and can be used for protecting a wide range of cultivated plants. Cyclothiazomycin C can be used to inhibit or destroy the fungi that occur on plants or parts of plants (fruit, blossoms, leaves, stems, tubers, roots) of different crops of useful plants, while at the same time protecting also those parts of the plants that grow later.

The present invention further relates to a method for controlling or preventing infestation of plants or plant propagation material and/or harvested food crops susceptible to fungal attack by treating plants or plant propagation material and/or harvested food crops wherein a fungicidally effective amount of cyclothiazomycin C is applied to the plants, to parts thereof or the locus thereof.

It is also possible to use cyclothiazomycin C more broadly as a fungicide. The term "fungicide" as used herein means a compound that controls, modifies, or prevents the growth of fungi. The term "fungicidally effective amount" where used means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It may also be possible to use cyclothiazomycin C as dressing agents for the treatment of plant propagation material, e.g., seed, such as fruits, tubers or grains, or plant cuttings, for the protection against fungal infections as well as against phytopathogenic fungi occurring in the soil. The propagation material can be treated with a composition comprising cyclothiazomycin C before planting: seed, for example, can be dressed before being sown. Cyclothiazomycin C can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Furthermore, cyclothiazomycin C can be used for controlling fungi in related areas, for example in the protection of technical materials, including wood and wood related technical products, in food preservation, in pharmaceutical applications, in veterinary applications and in hygiene management.

In addition, the invention could be used to protect non-living materials from fungal attack, e.g. lumber, wall boards, wallpaper and paint.

Examples of important fungi that require control in agriculture and other areas are:

*Albugo candida, Alternaria* spp.; *Alternaria alternate, Alternaria brassicae, Alternaria brassicicola, Alternaria solani, Alternaria tomatophila, Aphanomyces* spp.; *Aphanomyces cochlioides, Aphanomyces euteiches, Ascochyta* spp.; *Ascochyta pisi, Aspergillus* spp.; *Aspergillus carbonarius; Aspergillus flavus, Aspergillus niger, Blumeria* spp.; *Blumeria graminis* f. sp. *herdei, Blumeria graminis* f. sp. *tritici, Blumeriella jaapii, Botryosphaeria* spp.; *Botryosphaeria dothidea, Botryosphaeria obtusa, Botrytis* spp; *Botrytis cinerea, Bremia lactucae, Cadophora gregata, Ceratocystis* spp.; *Ceratocystis fimbriata Cercospora* spp.; *Cercospora beticola, Cercospora kikuchii, Cercospora sojina, Cercospora zeae-maydis, Cladosporium* spp; *Cladosporium cucumerinum, Clarireedia homoeocarpa, Claviceps purpurea, Cochliobolus* spp; *Cochliobolus carbonum, Cochliobolus heterostrophus, Cochliobolus lunatus, Cochliobolus miyabeanus, Cochliobolus sativus, Colletotrichum* spp; *Colletotrichum capsici, Colletotrichum coccodes, Colletotrichum dematium, Colletotrichum gloeosporioides, Colletotrichum graminicola, Colletotrichum lindemuthianum, Colletotrichum musae, Colletotrichum orbiculare, Colletotrichum truncatum, Corynespora cassiicola, Diaporthe* spp; *Diaporthe helianthi, Diaporthe longicolla Diaporthe neoviticola, Diaporthe sojae, Didymella* spp; *Drechslera* spp; *Drechslera gigantea, Elsinoe* spp; *Elsinoe glycines, Eremothecium gossypii, Erysiphe* spp; *Erysiphe cruciferarum, Erysiphe diffusa, Erysiphe necator, Eutypa lata, Fusarium* spp; *Fusarium culmorum, Fusarium langsethiae, Fusarium oxysporum* f. sp. *glycines, Fusarium oxysporum* f. sp. *vasinfectum, Fusarium oxysporum* f. sp. *betae, Fusarium oxysporum* f. sp. *cubense, Fusarium oxysporum* f. sp. *lycopersici, Fusarium poae, Fusarium proliferatum, Fusarium sacchari, Fusarium sporotrichioides, Fusarium tricinctum, Fusarium virguliforme, Gaeumannomyces graminis, Gibberella* spp; *Gibberella avenacea, Gibberella fujikuroi, Gibberella fujikuroi* var. *subglutinans, Gibberella intricans, Gibberella moniliformis, Gibberella zeae, Golovinomyces cichoracearum, Gymnosporangium juniperi-virginianae, Helminthosporium* spp; *Helminthosporium solani, Hemileia* spp; *Hemileia vastatrix, Hyaloperonospora parasitica, Kabatiella zeae, Laetisaria fuciformis, Leptographium lundbergii, Leveillula taurica, Lophodermium seditiosum, Microdochium majus, Monilinia* spp; *Monilinia fructicola, Monographella* spp; *Monographella albescens, Monographella nivalis, Mycosphaerella* spp; *Mycosphaerella arachidis, Mycosphaerella areola, Mycosphaerella berkeleyi, Mycosphaerella pomi, Nakataea oryzae, Neopseudocercosporella* spp; *Neopseudocercosporella brassicae, Neopseudocercosporella capsellae, Oculimacula yallundae, Ophiostoma* spp; *Ophiostoma piceae, Ophiostoma ulmi, Parastagonospora nodorum, Penicillium* spp; *Penicillium digitatum, Penicillium expansum, Penicillium italicum, Peronosclerospora* spp; *Peronosclerospora maydis, Peronosclerospora philippinensis, Peronosclerospora sorghi, Peronospora* spp; *Peronospora destructor, Peronospora manshurica, Phakopsora pachyrhizi, Phellinus igniarius, Phialophora* spp; *Phlyctema vagabunda, Phoma* spp; *Phyllachora* spp; *Phyllachora pomigena, Phyllosticta* spp; *Phyllosticta ampelicida, Phyllosticta citricarpa, Phyllosticta sphaeropsoidea, Physoderma maydis, Phytophthora* spp, *Phytophthora capsici, Phytophthora cinnamomi, Phytophthora infestans, Phytophthora sojae, Plasmodiophora brassicae, Plasmopara* spp; *Plasmopara halstedii, Plasmopara viticola, Plenodomus* spp; *Plenodomus biglobosus, Plenodomus lingam, Pleospora* spp; *Pleospora herbarum, Podosphaera* spp; *Podosphaera fusca, Podosphaera leucotricha, Podosphaera macularis, Pseudocercospora fijiensis, Pseudoperonospora* spp; *Pseudoperonospora cubensis, Pseudoperonospora humuli, Pseudopeziza tracheiphila, Pseudopyrenochaeta lycopersici, Puccinia* spp; *Puccinia allii, Puccinia graminis, Puccinia helianthi, Puccinia hordei, Puccinia kuehnii, Puccinia melanocephala, Puccinia polysora, Puccinia sorghi, Puccinia striiformis, Puccinia triticina, Pyrenopeziza* spp; *Pyrenopeziza brassicae, Pyrenophora* spp; *Pyrenophora graminea, Pyrenophora teres, Pyrenophora tritici-repentis, Pyricularia* spp; *Pyricularia graminis-tritici, Pyricularia oryzae, Pythium* spp; *Pythium aphanidermatum, Pythium sylvaticum, Pythium ultimum, Ramularia* spp; *Ramularia collo-cygni, Remotididymella destructiva, Rhizoctonia* spp; *Rhizoctonia cerealis, Rhizoctonia oryzae, Rhizoctonia oryzae-sativae, Rhizoctonia theobromae, Rhizopus arrhizus, Rhynchosporium* spp; *Rhynchosporium secalis, Sarocladium oryzae, Schizothyrium pomi, Sclerophthora macrospora, Sclerotinia* spp; *Sclerotinia sclerotiorum, Sclerotium* spp; *Septoria* spp; *Septoria glycines; Septoria lycopersici; Setosphaeria turcica; Sphaerotheca fuliginea, Stagonosporopsis cucurbitacearum, Stemphylium* spp; *Stemphylium solani, Stenocarpella macrospora, Stereum hirsutum, Thanatephorus cucumeris, Thielaviopsis basicola, Tilletia* spp; *Tilletia laevis, Tilletia tritici, Tranzschelia discolour, Trichoderma* spp; *Trichoderma viride, Typhula* spp; *Typhula incarnata, Urocystis* spp; *Urocystis agropyri, Urocystis colchici, Uromyces* spp; *Uromyces appendiculatus, Uromyces viciae-fabae, Ustilago* spp; *Ustilago maydis, Ustilago segetum* var. *hordei, Ustilago segetum* var. *nuda, Ustilago segetum* var. *tritici, Venturia* spp; *Venturia inaequalis, Venturia pyrina, Verticillium* spp; *Verticillium dahliae, Wilsonomyces carpophilus* and *Zymoseptoria tritici.*

Examples of other important fungi are *Absidia corymbifera, Aspergillus fumigatus, Emericella nidulans, Aspergillus terreus, Aureobasidium pullulans, Blastomyces dermatitidis, Candida albicans, Candida glabrata, Candida krusei, Candida lusitaniae, Candida parapsilosis, Candida tropicalis, Coccidioides immitis, Filobasidiella neoformans, Epidermophyton floccosum, Ajellomyces capsulatus, Microsporum* spp, *Mucor* spp, *Paracoccidioides* spp, *Petriellidium* spp, *Rhizomucor pusillus, Rhizopus arrhizus, Scedosporium* spp, *Pseudallescheria boydii, Scedosporium prolificans, Sporothorix* spp, *Trichophyton* spp, *Cephaloascus fragrans.*

Other plant pathogens include protists, for example *Polymyxa graminis* and *Polymyxa betae.*

Preferred examples are *Albugo candida, Alternaria alternata, Alternaria brassicae, Alternaria brassicicola, Alternaria tomatophila, Aphanomyces* spp.; *Aphanomyces cochlioides, *Aphanomyces euteiches*, *Ascochyta* spp.; *Ascochyta pisi*, *Aspergillus carbonarius*; *Aspergillus flavus*, *Blumeria graminis* f. sp. *herdei*, *Blumeriella jaapii*, *Botryosphaeria* spp.; *Botryosphaeria dothidea*, *Botryosphaeria obtusa*, *Botrytis* spp; *Botrytis cinerea*, *Bremia lactucae*, *Cadophora gregata*, *Ceratocystis* spp.; *Ceratocystis fimbriata*, *Cercospora* spp.; *Cercospora beticola*, *Cercospora kikuchii*, *Cercospora sojina*, *Cercospora zeae-maydis*, *Cladosporium* spp; *Cladosporium cucumerinum*, *Clarireedia homoeocarpa*, *Claviceps purpurea*, *Cochliobolus* spp; *Cochliobolus carbonum*, *Cochliobolus heterostrophus*, *Cochliobolus lunatus*, *Cochliobolus miyabeanus*, *Cochliobolus sativus*, *Colletotrichum* spp; *Colletotrichum capsica*, *Colletotrichum coccodes*, *Colletotrichum dematium*, *Colletotrichum gloeosporioides*, *Colletotrichum graminicola*, *Colletotrichum lindemuthianum*, *Colletotrichum musae*, *Colletotrichum orbiculare*, *Colletotrichum truncatum*, *Corynespora cassiicola*, *Diaporthe* spp; *Diaporthe helianthi*, *Diaporthe longicolla* *Diaporthe neoviticola*, *Diaporthe sojae*, *Didymella* spp; *Drechslera* spp; *Drechslera gigantea*, *Elsinoe* spp; *Elsinoe glycines*, *Eremothecium gossypii*, *Erysiphe* spp; *Erysiphe cruciferarum*, *Erysiphe diffusa*, *Erysiphe necator*, *Eutypa lata*, *Fusarium langsethiae*, *Fusarium oxysporum* f. sp. *glycines*, *Fusarium oxysporum* f. sp. *vasinfectum*, *Fusarium oxysporum* f. sp. *betae*, *Fusarium oxysporum* f. sp. *cubense*, *Fusarium oxysporum* f. sp. *lycopersici*, *Fusarium poae*, *Fusarium proliferatum*, *Fusarium sacchari*, *Fusarium sporotrichioides*, *Fusarium tricinctum*, *Fusarium virguliforme*, *Gaeumannomyces graminis*, *Gibberella* spp; *Gibberella avenacea*, *Gibberella fujikuroi*, *Gibberella fujikuroi* var. *subglutinans*, *Gibberella intricans*, *Gibberella moniliformis*, *Gibberella zeae*, *Golovinomyces cichoracearum*, *Gymnosporangium juniperi-virginianae*, *Helminthosporium* spp; *Helminthosporium solani*, *Hemileia* spp; *Hemileia vastatrix*, *Hyaloperonospora parasitica*, *Kabatiella zeae*, *Laetisaria fuciformis*, *Leptographium lundbergii*, *Leveillula taurica*, *Lophodermium seditiosum*, *Microdochium majus*, *Monilinia* spp; *Monilinia fructicola*, *Monographella* spp; *Monographella albescens*, *Monographella nivalis*, *Mycosphaerella* spp; *Mycosphaerella arachidis*, *Mycosphaerella areola*, *Mycosphaerella berkeleyi*, *Mycosphaerella pomi*, *Nakataea oryzae*, *Neopseudocercosporella* spp; *Neopseudocercosporella brassicae*, *Neopseudocercosporella capsellae*, *Oculimacula yallundae*, *Ophiostoma piceae*, *Ophiostoma ulmi*, *Penicillium* spp; *Penicillium digitatum*, *Penicillium expansum*, *Penicillium italicum*, *Peronosclerospora* spp; *Peronosclerospora maydis*, *Peronosclerospora philippinensis*, *Peronosclerospora sorghi*, *Peronospora* spp; *Peronospora destructor*, *Peronospora manshurica*, *Phakopsora pachyrhizi*, *Phellinus igniarius*, *Phialophora* spp; *Phlyctema vagabunda*, *Phoma* spp; *Phyllachora* spp; *Phyllachora pomigena*, *Phyllosticta* spp; *Phyllosticta ampelicida*, *Phyllosticta citricarpa*, *Phyllosticta sphaeropsoidea*, *Physoderma maydis*, *Phytophthora* spp, *Phytophthora capsici*, *Phytophthora cinnamomi*, *Phytophthora infestans*, *Phytophthora sojae*, *Plasmodiophora brassicae*, *Plasmopara* spp; *Plasmopara halstedii*, *Plasmopara viticola*, *Plenodomus* spp; *Plenodomus biglobosus*, *Plenodomus lingam*, *Pleospora* spp; *Pleospora herbarum*, *Podosphaera* spp; *Podosphaera fusca*, *Podosphaera leucotricha*, *Podosphaera macularis*, *Pseudocercospora fijiensis*, *Pseudoperonospora* spp; *Pseudoperonospora cubensis*, *Pseudoperonospora humuli*, *Pseudopeziza tracheiphila*, *Pseudopyrenochaeta lycopersici*, *Puccinia* spp; *Puccinia allii*, *Puccinia graminis*, *Puccinia helianthi*, *Puccinia hordei*, *Puccinia kuehnii*, *Puccinia melanocephala*, *Puccinia polysora*, *Puccinia sorghi*, *Puccinia striiformis*, *Puccinia triticina*, *Pyrenopeziza* spp; *Pyrenopeziza brassicae*, *Pyrenophora graminea*, *Pyrenophora tritici-repentis*, *Pyricularia graminis-tritici*, *Pythium* spp; *Pythium aphanidermatum*, *Pythium sylvaticum*, *Pythium ultimum*, *Ramularia* spp; *Ramularia collo-cygni*, *Remotididymella destructive*, *Rhizoctonia* spp; *Rhizoctonia cerealis*, *Rhizoctonia oryzae*, *Rhizoctonia oryzae-sativae*, *Rhizoctonia theobromae*, *Rhizopus arrhizus*, *Rhynchosporium* spp; *Rhynchosporium secalis*, *Sarocladium oryzae*, *Schizothyrium pomi*, *Sclerophthora macrospora*, *Sclerotium* spp; *Septoria* spp; *Septoria glycines*; *Septoria lycopersici*; *Setosphaeria turcica*; *Sphaerotheca fuliginea*, *Stagonosporopsis cucurbitacearum*, *Stemphylium* spp; *Stemphylium solani*, *Stenocarpella macrospora*, *Stereum hirsutum*, *Thielaviopsis basicola*, *Tilletia* spp; *Tilletia laevis*, *Tilletia tritici*, *Tranzschelia discolour*, *Trichoderma* spp; *Trichoderma viride*, *Typhula* spp; *Typhula incarnata*, *Urocystis* spp; *Urocystis agropyri*, *Urocystis colchici*, *Uromyces* spp; *Uromyces appendiculatus*, *Uromyces viciae fabae*, *Ustilago* spp; *Ustilago maydis*, *Ustilago segetum* var. *hordei*, *Ustilago segetum* var. *nuda*, *Ustilago segetum* var. *tritici*, *Venturia* spp; *Venturia inaequalis*, *Venturia pyrina*, *Verticillium* spp; *Verticillium dahliae*, *Wilsonomyces carpophilus*, *Zymoseptoria tritici*, *Absidia corymbifera*, *Aspergillus fumigatus*, *Emericella nidulans*, *Aspergillus terreus*, *Aureobasidium pullulans*, *Blastomyces dermatitidis*, *Candida albicans*, *Candida glabrata*, *Candida krusei*, *Candida lusitaniae*, *Candida parapsilosis*, *Candida tropicalis*, *Coccidioides immitis*, *Filobasidiella neoformans*, *Epidermophyton floccosum*, *Ajellomyces capsulatus*, *Microsporum* spp, *Mucor* spp, *Paracoccidioides* spp, *Petriellidium* spp, *Rhizomucor pusillus*, *Rhizopus arrhizus*, *Scedosporium* spp, *Pseudallescheria boydii*, *Scedosporium prolificans*, *Sporothorix* spp, *Trichophyton* spp, *Cephaloascus fragrans*, *Polymyxa graminis*, *Polymyxa betae*.

More preferred examples of fungi are *Botrytis cinerea*, *Bremia lactucae*, *Cercospora beticola*, *Cercospora kikuchii*, *Cercospora sojina*, *Colletotrichum dematium*, *Colletotrichum lindemuthianum*, *Colletotrichum orbiculare*, *Colletotrichum truncatum*, *Corynespora cassiicola*, *Erysiphe cruciferarum*, *Erysiphe necator*, *Fusarium virguliforme*, *Gibberella zeae*, *Golovinomyces cichoracearum*, *Microdochium majus*, *Monilinia fructicola*, *Monographella nivalis* *Mycosphaerella arachidis*, *Peronospora destructor*, *Phakopsora pachyrhizi*, *Phytophthora capsici*, *Phytophthora infestans*, *Plasmopara halstedii*, *Plasmopara viticola*, *Pseudocercospora fijiensis*, *Pseudoperonospora cubensis*, *Puccinia triticina*, *Sphaerotheca fuliginea*, *Venturia inaequalis* and *Zymoseptoria tritici*.

Still more preferred examples of fungi are *Botrytis cinerea*, *Cercospora kikuchii*, *Cercospora sojina*, *Cochliobolus sativus*, *Colletotrichum lindemuthianum*, *Colletotrichum orbiculare*, *Corynespora cassiicola*, *Fusarium avenaceum*, *Fusarium culmorum*, *Fusarium langsethiae*, *Fusarium poae*, *Fusarium sporotrichioides*, *Fusarium tricinctum*, *Fusarium virguliforme*, *Gibberella avenacea*, *Gibberella fujikuroi*, *Gibberella zeae*, *Microdochium majus*, *Monographella nivalis*, *Mycosphaerella arachidis*, *Phakopsora pachyrhizi*, *Puccinia triticina*, *Pyrenophora tritici-repentis*, *Ramularia collo-cygni*, *Rhynchosporium secalis*, *Septoria glycines*, *Tilletia tritici*, *Ustilago segetum* var. *Tritici*, *Venturia inaequalis*, and *Zymoseptoria tritici*.

Most preferred examples of fungi are *Botrytis cinerea* (also known as *Botryotinia fuckeliana* or Grey Mould), *Fusarium virguliforme* (also known as *Fusarium solani* f. sp. *glycines* or sudden death syndrome of soybean) *Monographella nivalis* (also known as *Microdichium nivale* or Cereal Head Blight), *Mycosphaerella arachidis* (also known as *Cercospora arachidicola* or Groundnut Brown Leaf Spot), *Phakopsora pachyrhizi* (also known as Asian Soybean Rust), *Puccinia* triticina (also known as *Puccinia recondita* f. sp. *tritici* or wheat brown leaf rust) and *Zymoseptoria tritici* (also known as *Septoria tritici, Mycosphaerella graminicola* or *Septoria* Leaf Blotch).

Target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum, triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and *Zoysia* grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as also including useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enolpyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as also including useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or Xenorhabdus spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as plant lectins, such as pea lectins, barley lectins or snowdrop lectins; agglutinins; proteinase inhibitors, such as trypsin inhibitors, serine protease inhibitors, patatin, cystatin, papain inhibitors; ribosomeinactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

Further, in the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO93/07278, WO95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are Bt11 Maize from Syngenta, Bt176 Maize from Syngenta, MIR604 Maize from Syngenta, MON 863 Maize from Monsanto, IPC 531 Cotton from Monsanto, 1507 Maize from Pioneer, NK603×MON 810 Maize from Monsanto.

Cyclothiazomycin C may also be used for example on turf, ornamentals, such as flowers, shrubs, broad-leaved trees or evergreens, for example conifers, as well as for tree injection, pest management and the like.

Preferred crops on which Cyclothiazomycin C can be used include soybean and cereals, particularly wheat.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There can be mentioned for example seeds (in the strict sense), roots, fruits, tubers, bulbs, rhizomes and parts of plants. Germinated plants and young plants which are to be transplanted after germination or after emergence from the soil, may also be mentioned. These young plants can be protected before transplantation by a total or partial treatment by immersion. Preferably "plant propagation material" is understood to denote seeds.

Cyclothiazomycin C may be used in unmodified form or, preferably, together with the adjuvants conventionally employed in the art of formulation. To this end it may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Furthermore, when cyclothiazomycin C is obtained from a microorganism, it may be isolated from that microorganism as described in WO2015191789. Alternatively, there may be significant quantities of cyclothiazomycin C in the culture medium in which the microorganism is grown in which case a fungicidal composition can be formulated using the culture medium, or broth. As a further alternative, the microorganism itself can be used to formulate a composition. In such cases the microorganism can be formulated as living cells actively producing cyclothiazomycin C or it can be inactivated, for example by heat treatment. The microorganism can be concentrated if necessary, by centrifuge or other conventional techniques.

Suitable carriers and adjuvants, e.g. for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

Suspension concentrates are aqueous formulations in which finely divided solid particles of the active compound are suspended. Such formulations include anti-settling agents and dispersing agents and may further include a wetting agent to enhance activity as well an anti-foam and a crystal growth inhibitor. In use, these concentrates are diluted in water and normally applied as a spray to the area to be treated. The amount of active ingredient may range from 0.5% to 95% of the concentrate.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain from 5% to 95% of the active ingredient plus a small amount of wetting, dispersing or emulsifying agent.

Emulsifiable concentrates are homogeneous liquid compositions dispersible in water or other liquid and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from 0.5% to 95% of the concentrate.

Granular formulations include both extrudates and relatively coarse particles and are usually applied without dilution to the area in which treatment is required. Typical carriers for granular formulations include sand, fuller's earth, attapulgite clay, bentonite clays, montmorillonite clay, vermiculite, perlite, calcium carbonate, brick, pumice, pyrophyllite, kaolin, dolomite, plaster, wood flour, ground corn cobs, ground peanut hulls, sugars, sodium chloride, sodium sulphate, sodium silicate, sodium borate, magnesia, mica, iron oxide, zinc oxide, titanium oxide, antimony oxide, cryolite, gypsum, diatomaceous earth, calcium sulphate and other organic or inorganic materials which absorb or which can be coated with the active compound. Granular formulations normally contain 5% to 25% of active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active ingredient enclosed in an inert porous shell which allows escape of the enclosed material to the surroundings at controlled rates. Encapsulated droplets are typically 1 to 50 microns in diameter. The enclosed liquid typically constitutes 50 to 95% of the weight of the capsule and may include solvent in addition to the active compound. Encapsulated granules are generally porous granules with porous membranes sealing the granule pore openings, retaining the active species in liquid form inside the granule pores. Granules typically range from 1 millimetre to 1 centimetre and preferably 1 to 2 millimetres in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for agrochemical applications include simple solutions of the active ingredient in a solvent in which it is completely soluble at the desired concentration, such as acetone, alkylated naphthalenes, xylene and other organic solvents. Pressurised sprayers, wherein the active ingredient is dispersed in finely-divided form as a result of vaporisation of a low boiling dispersant solvent carrier, may also be used.

Suitable agricultural adjuvants and carriers that are useful in formulating the compositions of the invention in the formulation types described above are well known to those skilled in the art.

Liquid carriers that can be employed include, for example, water, toluene, xylene, petroleum naphtha, crop oil, acetone, methyl ethyl ketone, cyclohexanone, acetic anhydride, acetonitrile, acetophenone, amyl acetate, 2-butanone, chlorobenzene, cyclohexane, cyclohexanol, alkyl acetates, diacetonalcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethyl formamide, dimethyl sulfoxide, 1,4-dioxane, dipropylene glycol, dipropylene glycol methyl ether, dipropylene glycol dibenzoate, diproxitol, alkyl pyrrolidinone, ethyl acetate, 2-ethyl hexanol, ethylene carbonate, 1,1,1-trichloroethane, 2-heptanone, alpha pinene, d-limonene, ethylene glycol, ethylene glycol butyl ether, ethylene glycol methyl ether, gamma-butyrolactone, glycerol, glycerol diacetate, glycerol monoacetate, glycerol triacetate, hexadecane, hexylene glycol, isoamyl acetate, isobornyl acetate, isooctane, isophorone, isopropyl benzene, isopropyl myristate, lactic acid, laurylamine, mesityl oxide, methoxy-propanol, methyl isoamyl ketone, methyl isobutyl ketone, methyl laurate, methyl octanoate, methyl oleate, methylene chloride, m-xylene, n-hexane, n-octylamine, octadecanoic acid, octyl amine acetate, oleic acid, oleylamine, o-xylene, phenol, polyethylene glycol (PEG400), propionic acid, propylene glycol, propylene glycol monomethyl ether, p-xylene, toluene, triethyl phosphate, triethylene glycol, xylene sulfonic acid, paraffin, mineral oil, trichloroethylene, perchloroethylene, ethyl acetate, amyl acetate, butyl acetate, methanol, ethanol, isopropanol, and higher molecular weight alcohols such as amyl alcohol, tetrahydrofurfuryl alcohol, hexanol, octanol, etc., ethylene glycol, propylene glycol, glycerine and N-methyl-2-pyrrolidinone. Water is generally the carrier of choice for the dilution of concentrates.

Suitable solid carriers include, for example, talc, titanium dioxide, pyrophyllite clay, silica, attapulgite clay, kieselguhr, chalk, diatomaxeous earth, lime, calcium carbonate, bentonite clay, fuller's earth, cotton seed hulls, wheat flour, soybean flour, pumice, wood flour, walnut shell flour and lignin.

A broad range of surface-active agents are advantageously employed in both said liquid and solid compositions, especially those designed to be diluted with carrier before application. These agents, when used, normally comprise from 0.1% to 15% by weight of the formulation. They can be anionic, cationic, non-ionic or polymeric in character and can be employed as emulsifying agents, wetting agents, suspending agents or for other purposes. Typical surface active agents include salts of alkyl sulfates, such as diethanolammonium lauryl sulphate; alkylarylsulfonate salts, such as calcium dodecylbenzenesulfonate; alkylphenol-alkylene oxide addition products, such as nonylphenol-C.sub. 18 ethoxylate; alcohol-alkylene oxide addition products, such as tridecyl alcohol-C.sub. 16 ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include crystallisation inhibitors, viscosity modifiers, suspending agents, spray droplet modifiers, pigments, antioxidants, foaming agents, anti-foaming agents, light-blocking agents, compatibilizing agents, antifoam agents, sequestering agents, neutralising agents and buffers, corrosion inhibitors, dyes, odorants, spreading agents, penetration aids, micronutrients, emollients, lubricants and sticking agents.

In addition, further, other biocidally active ingredients or compositions may be combined with the compositions of the invention and used in the methods of the invention and applied simultaneously or sequentially with the compositions of the invention. When applied simultaneously, these further active ingredients may be formulated together with the compositions of the invention or mixed in, for example, the spray tank. These further biocidally active ingredients may be fungicides, herbicides, insecticides, bactericides, acaricides, nematicides and/or plant growth regulators.

Pesticidal agents are referred to herein using their common name are known, for example, from "The Pesticide Manual", 15th Ed., British Crop Protection Council 2009.

In addition, the compositions of the invention may also be applied with one or more systemically acquired resistance inducers ("SAR" inducer). SAR inducers are known and described in, for example, U.S. Pat. No. 6,919,298 and include, for example, salicylates and the commercial SAR inducer acibenzolar-S-methyl.

Cyclothiazomycin C is normally used in the form of an agrochemical composition and can be applied to the crop area or plant to be treated, simultaneously or in succession with further compounds. These further compounds can be e.g. fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

Cyclothiazomycin C may be used in the form of (fungicidal) compositions for controlling or protecting against phytopathogenic microorganisms, comprising as active ingredient cyclothiazomycin C and at least one of the above-mentioned adjuvants.

The invention therefore provides a composition, preferably a fungicidal composition, comprising cyclothiazomycin C, an agriculturally acceptable carrier and optionally an adjuvant. An agricultural acceptable carrier is for example a carrier that is suitable for agricultural use. Agricultural carriers are well known in the art. Preferably said composition may comprise at least one or more pesticidally-active compounds, for example an additional fungicidal active ingredient in addition to cyclothiazomycin C.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds (I) for the preparation of these compositions are also a subject of the invention.

Another aspect of the invention is related to the use of a composition comprising cyclothiazomycin C, or of a fungicidal or insecticidal mixture comprising cyclothiazomycin C, in admixture with other fungicides or insecticides as described above, for controlling or preventing infestation of plants, e.g. useful plants such as crop plants, propagation material thereof, e.g. seeds, harvested crops, e.g. harvested food crops, or non-living materials by insects or by phytopathogenic microorganisms, preferably fungal organisms.

A further aspect of the invention is related to a method of controlling or preventing an infestation of plants, e.g., useful plants such as crop plants, propagation material thereof, e.g. seeds, harvested crops, e.g., harvested food crops, or of non-living materials by insects or by phytopathogenic or spoilage microorganisms or organisms potentially harmful to man, especially fungal organisms, which comprises the application of cyclothiazomycin C as active ingredient to the plants, to parts of the plants or to the locus thereof, to the propagation material thereof, or to any part of the non-living materials.

Controlling or preventing means reducing infestation by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of Formula (I), or an agrochemical composition which contains at least one of said compounds, is foliar application. The frequency of application and the rate of application will depend on the risk of infestation by the corresponding pathogen. However, the compounds of Formula (I) can also penetrate the plant through the roots via the soil by drenching the locus of the plant with a liquid Formulation, or by applying the compounds in solid form to the soil, e.g. in granular form (soil application). In crops of water rice such granulates can be applied to the flooded rice field. The compounds of Formula (I) may also be applied to seeds (coating) by impregnating the seeds or tubers either with a liquid formulation of the fungicide or coating them with a solid formulation.

A formulation, e.g. a composition containing the compound of Formula (I), and, if desired, a solid or liquid adjuvant or monomers for encapsulating the compound of Formula (I), may be prepared in a known manner, typically by intimately mixing and/or grinding the compound with extenders, for example solvents, solid carriers and, optionally, surface active compounds (surfactants).

Advantageous rates of application are normally from 5 g to 6 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

When the combinations of the present invention are used for treating seed, rates of 0.001 to 50 g of cyclothiazomycin C per kg of seed, preferably from 0.01 to 10 g per kg of seed are generally sufficient.

Suitably, a composition comprising cyclothiazomycin C according to the present invention is applied either preventative, meaning prior to disease development or curative, meaning after disease development.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g. by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly Formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g. as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), cyclothiazomycin C optionally together with other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

Another aspect of the invention is related to use of cyclothiazomycin C as an anti fungal agent in food, feed, beverages or in cosmetic products. Preferably, wherein the food products are fruits and fruit derived products, vegetable and vegetable derived products, grain and grain derived products, dairy products, meat, poultry and seafood and mixtures thereof. Preferably, wherein the food is chosen from dairy products or baking products. Preferably the dairy product is a fermented dairy product such as yoghurt or cheese. More preferably wherein the dairy product is chosen from the group consisting of yogurt, low fat yogurt, non fat yogurt, kefir, dahi, ymer, buttermilk, butter, sour cream, sour whipped cream, fresh cheeses, unripened cheeses or curd cheeses and ripened cheese. Preferably, the present invention relates to the use of cyclothiazomycin C as an anti fungal agent, wherein the fungi is chosen from the group consisting of (Aspergillus), Aspergillus, Penicillium (Penicillium), Cladosporium (Cladosporium), Rhizopus (Rhizopus), Eurotium (Eurotium), Paecilomyces (Paecilomyces), Saccharomyces (Saccharomyces), Zygosaccharomyces (Zygosaccharomyces), Debaryomyces (Debaryomyces), Candida (Candida), Rhizopus (Rhizopus), Fusarium (Fusarium), Altemaria (Altemaria) and Mucor (Mucor). More preferably, the present invention relates to the use of cyclothiazomycin C as an anti fungal agent in baking products, wherein the fungi is chosen from the group consisting of Aspergillus niger, Aspergillus fumigatus, Aspergillus flavus, Eurotium rubrum, Paecilomyces variotii, Penicillium roquefori.

More preferably, the present invention relates to the use of cyclothiazomycin C as an anti fungal agent in beverages, wherein the fungi is chosen from the group consisting of Aspergillus niger, Saccharomyces cerevisiae and Zygosaccharomyces bailii.

More preferably, the present invention relates to the use of cyclothiazomycin C as an anti fungal agent in dairy products as defined above, wherein the fungi is chosen from the group consisting of Klyveromyces marxianus, Yarrowia lipolytica, Penicillium nalgiovense, Cladiosporium ssp., Penicillium commune, Mucor ssp., Penicillium brevicompactum, Aspergillus versicolor, Penicillium crustosum, Kluyveromyces lactis, more preferably, wherein the fungi is Penicillium roquefori or is Debaryomyces hansenii.

The cyclothiazomycin C can be used in several ways to provide an anti fungal effect. Preferably, the cyclothiazomycin C is dosed in an effective amount. The cyclothiazomycin C may be added in a final stage or in intermediate stages of producing a food, a feed, a beverage or a cosmetic product. Preferably, the surface of the food, feed, beverage or the cosmetic product is treated with the cyclothiazomycin C. For example, the cyclothiazomycin C is sprayed or coated on the surface of the food, feed, beverages or cosmetic product. For example, the cyclothiazomycin is sprayed or coated on a dairy product, such as yogurt or on cheese for example. Alternatively, the cyclothiazomycin C is mixed with the food, feed, beverages or cosmetic product. For example, the cyclothiazomycin C is blended with a dairy product, such as milk or yogurt. Alternatively, the cyclothiazomycin C is blended in a dough for the preparation of baking products.

Cyclothiazomycin C may be used in unmodified form or, preferably, may be formulated as defined above. Preferably, a composition comprising cyclothiazomycin C comprises adjuvants, surface active agents, solid carriers and/or liquid carriers all as defined above. As a further alternative, the microorganism itself can be used to formulate a composition. In such cases the microorganism can be formulated as living cells actively producing cyclothiazomycin C or it can be inactivated, for example by heat treatment. The microorganism can be concentrated if necessary, by centrifuge or other conventional techniques.

According to a further aspect, the present invention relates to cyclothiazomycin C for use as a medicament. Further, the present invention relates to Cyclothiazomycin C for use as a pharmaceutical product for treating infections with pathogenic fungi, preferably pathogenic yeasts. In a preferred embodiment the pharmaceutical product is a product useful for administration of the cyclothiazomycin C to a human or an animal to inhibit pathogenic microorganisms and alleviating symptoms related to the pathogenic microorganisms. Examples of such symptoms include symptoms related to yeast infection. In such an embodiment, the pharmaceutical product may be a unit dosage form comprising cyclothiazomycin C. Preferably, the unit dosage form is a capsule or a tablet. However, the unit dosage form may also be suitable for application to the mucosa or skin and, thus, be in the form of a paste, cream, ointment and the like.

EXAMPLES

The Examples which follow serve to illustrate the invention.

Throughout this description, temperatures are given in degrees Celsius (° C.) and "mp." means melting point and rh means relative humidity. LC/MS means Liquid Chromatography Mass Spectrometry and the description of the apparatus and the method is as follows:

Example 1: Isolation of Cyclothiazomycin C from NRRL WC-9803

NRRL strain WC-3908 obtained from the NRRL culture collection and was cultured in a 100 mL baffled shake flask at 225 rpm in an Innova 44 shaker incubator, stroke 1 inch. The flask contained 25 mL of medium with 10 g/L Merck casein hydrolysate, 8 g/L Difco Bacto tryptone, 2 g/L Difco Bacto Soytone, 1.25 g/L $K_2HPO_4$, and 0.3 g/L Basildon antifoam. The flask was closed with a foam plug. Prior to autoclaving, the pH was adjusted to 6.8 with 4 N $H_2SO_4$. From a separately autoclaved 500 g/L glucose.$H_2O$ stock, 15 g/L glucose.$H_2O$ was added. Inoculation was with biomass or spores and incubation at 28° C. was continued until glucose was between 1 and 5 g/L, requiring approx. 2 to 3 days.

This broth was spotted directly on bioassay plates in 7 µl droplets. Furthermore, extracts were made by freeze drying 1 mL and extraction with 1 mL 80% (w/v) acetonitrile. Of the extracts, 5 µl was spotted. As negative controls, sterile medium was used in the case of the broth containing living cells, or 80% acetonitrile in the case of the extract.

Example 2: Plate Bioassay Against *Botrytis cinerea* and *Zymoseptoria tritici*

Preparation of the Bioassay Plates.

The medium for the bioassay plates was prepared by mixing equal volumes of Difco Plate Count Agar and Difco Potato Dextrose Agar. 40 mL was used in Nunc™ Omni-Tray™ Single-Well Plates. After solidification and cooling to 20° C., 10 mL top-layer was applied containing equal amounts of sterile water and Difco Potato Dextrose Agar, at 42° C. Just before pouring the top-layer, spores of *Fusarium culmorum, Botrytis cinerea* or *Zymoseptoria tritici* were added. The spore concentrations used were 1000 cfu/mL for *B. cinerea*, and 20,000 cfu/mL for *Z. tritici*. After pouring the top-layers, the bioassay plates were dried in laminar flow cabinet for 1 hour and used immediately. After applying the samples, the plates were incubated at 22° C. until the fungi allowed visual assessment of the zone of inhibition.

The broth of example 1 was added to the bioassay plates as 7 µl droplets.

An example of the zones of inhibition found is given in FIG. 1A showing a zone of inhibition caused by a whole broth sample of NRRL strain WC-3908 on a *Botrytis cinerea* bioassay plate.

Figure 1B:
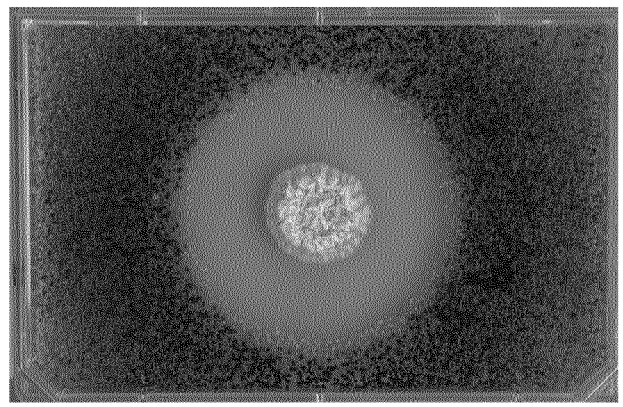

An example of the zones of inhibition found is given in FIG. 1B showing a zone of inhibition caused by a whole broth sample of NRRL strain WC-3908 on a *Zymoseptoria tritici* bioassay plate.

Figure 1C:
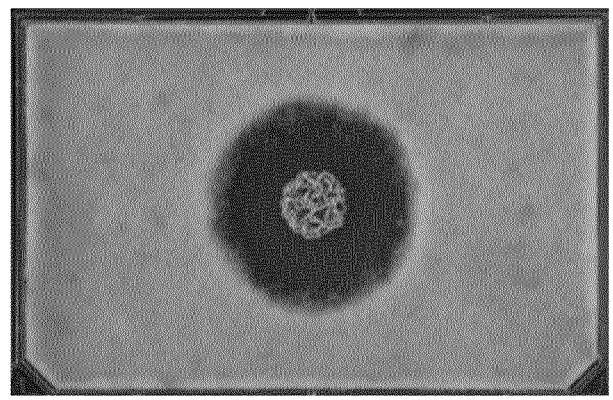

An example of the found zones of inhibition is given in FIG. 1C showing a zone of inhibition caused by a whole broth sample of NRRL strain WC-3908 on a *Fusarium culmorum* bioassay plate.

Example 3: Efficacy of Purified CtmC on *Fusarium Virguliforme*

A *Fusarium virguliforme* spore suspension of 25'000 spores/ml was produced in PDB (potato dextrose broth) medium supplemented with 0.3% agar. Isolates of the species originate from Syngenta internal collection (CH).

CtmC was dissolved in DMSO (Dimethylsulfoxid) to a final concentration of 1000 ppm to create a stock solution. Different dilutions of CtmC were created in DMSO: 1000 ppm, 330 ppm, 110 ppm, 37 ppm, 12 ppm and 4.1 ppm. 10 μl of DMSO or CtmC solution were transferred to a 96-well-dilution plate and diluted 10-fold with 90 μl 0.025% Tween 20/H2O solution. Out of the dilution plate, 10 μl were transferred to a 96 well assay plate and 90 μl spore suspension were added to each well.

Wells of 96 well plates contain the following:

TABLE 1

| well | medium (ul) + 0.0025% Tween/H2O | DMSO (ul) | CtmC (ppm) | spores |
|---|---|---|---|---|
| A | 90 + 9 | 1 | 0 | no |
| B | 90 + 9 | 1 | 10 | yes |
| C | 90 + 9 | 1 | 3.3 | yes |
| D | 90 + 9 | 1 | 1.1 | yes |
| E | 90 + 9 | 1 | 0.37 | yes |
| F | 90 + 9 | 1 | 0.12 | yes |
| G | 90 + 9 | 1 | 0.04 | yes |
| H | 90 + 9 | 1 | 0 | Yes |

96 Well plates were then incubated for 72 h at 24° C., 90% relative humidity in the dark. Plates were evaluated by reading the OD at 620 nm.

Assays were run on two independent isolates for the species. Each isolate was tested twice (assay 1 and assay 2) and each isolate×fungicide rate combination was duplicated on the test plates.

The OD620 was averaged over the two wells and used to calculate IC50 values (fungicide concentration resulting in 50% inhibition of growth) with the program GraphPad prism, resulting in 4 independent IC50 values. No significant differences were found between both isolates tested:

TABLE 2

| species and IC50 (ppm) | Assay-1 | Assay-2 | average |
|---|---|---|---|
| *Fusarium virguliforme* isolate 1 | 0.8 | 1.6 | 1.2 |
| *Fusarium virguliforme* isolate 2 | 0.7 | 1.5 | 1.1 |

As shown in table 2 above, both tested isolates have a similar IC50 of ca. 1 ppm.

Example 4: Efficacy of Purified CtmC on Fungal Species In-Vitro

CtmC was dissolved in DMSO (Dimethylsulfoxid) to a final concentration of 1000 ppm to create a stock solution. A second dilutions of 1:10 was made in water+0.025% Tween 20. From this second dilution 10 ul are dispensed into a 96 well plate. To each well, 90 ul of medium with fungal spores are added and mixed, resulting in final CtmC concentrations of 10 ppm. All wells containing CtmC also contain DMSO (1%) and Tween 20 (0.0025%).

*Botrytis cinerea* (gray mould): Conidia of the fungus from cryogenic storage were directly mixed into nutrient broth (PDB potato dextrose broth). After placing a solution of the test compounds into a microtiter plate (96-well format) the nutrient broth containing the fungal spores was added. The test plates were incubated at 24° C. and the inhibition of growth was determined photometrically after 72 hrs.

*Monographella nivalis* (snow mould, foot rot of cereals): Conidia of the fungus from cryogenic storage were directly mixed into nutrient broth (PDB potato dextrose broth). After placing a solution of the test compounds into a microtiter plate (96-well format) the nutrient broth containing the fungal spores was added. The test plates were incubated at 24° C. and the inhibition of growth was determined photometrically after 72 hrs at 620 nm.

*Mycosphaerella arachidis* (Brown leaf spot of groundnut): Conidia of the fungus from cryogenic storage were directly mixed into nutrient broth (PDB potato dextrose broth). After placing a solution of the test compounds into a microtiter plate (96-well format) the nutrient broth containing the fungal spores was added. The test plates were incubated at 24° C. and the inhibition of growth was determined photometrically after approximately 5-6 days at 620 nm.

*Zymoseptoria tritici* (*Septoria* leaf blotch): Conidia of the fungus from cryogenic storage were directly mixed into nutrient broth (PDB potato dextrose broth). After placing a solution of the test compounds into a microtiter plate (96-well format) the nutrient broth containing the fungal spores was added. The test plates were incubated at 24° C. and the inhibition of growth was determined photometrically after 72 hrs.

| compounds and control of fungal growth (%) | rate | Botrytis cinerea | Monographella nivalis | Mycosphaerella arachidis | Zymoseptoria tritici |
|---|---|---|---|---|---|
| Cyclothiazomycin C | 10 ppm | 90 | 100 | 100 | 90 |
| Water | — | 0 | 0 | 0 | 0 |

Conidial spores of 4 species tested were prevented from growth in presence of 10 ppm of Cyclothiazomycin C (reduction by 90-100%).

Example 5: Efficacy of Purified CtmC on Fungal Species in a Leaf Disc Assay

A CtmC stock was generated at 1000 ppm in DMSO, then Diluted 1:50 in water+Tween 20 at 0.025% resulting in a 20 ppm solution.

*Puccinia triticina* (also known as recondite, Brown rust, wheat): Wheat leaf segments are placed on agar in multiwell plates (24-well format) and sprayed with test solutions. After drying, the leaf disks are inoculated with a spore suspension of the fungus. After appropriate incubation the activity of a compound is assessed 8 dpi (days after inoculation) as preventive fungicidal activity.

*Phakopsora pachyrhizi* (Asian Soybean rust): Soybean leaf disks are placed on agar in multiwell plates (24-well format) and sprayed with test solutions. After drying, the leaf disks are inoculated with a spore suspension of the fungus. After appropriate incubation the activity of a compound is assessed approx. 12 dpi (days after inoculation) as preventive fungicidal activity

| compound and control of fungal growth (%) | rate | Puccinia triticina | Phakopsora pachyrhizi |
|---|---|---|---|
| Cyclothiazomycin C | 20 ppm | 90 | 50 |
| Water | — | 0 | 0 |

CtmC at 20 ppm was able to reduce development of two tested rust species by 50-90%.

Example 6: Efficacy of Purified CtmC on Fungal Species in the Greenhouse

Purified Cyclothiazomycin C (CtmC) was formulated as an EC50 formulation. The formulation was diluted in water at rates of 100 ppm and 50 ppm of CtmC. Plants were treated with 400 L/ha of the diluted product supplemented with an adjuvant to improve sticking and spreading, resulting in a treatment of 40 g/ha and 20 g/ha of CtmC, respectively.

*Zymoseptoria tritici* wheat/preventative (*Septoria tritici* leaf spot on wheat). 2-week old wheat plants cv. Riband are sprayed in a spray chamber with the formulated test compound diluted in water. The test plants are inoculated by spraying a spore suspension on them one day after application. After an incubation period of 1 day at 22° C./21° C. (day/night) and 95% rh, the inoculated test plants are kept at 22° C./21° C. (day/night) and 70% rh in a greenhouse. Efficacy is assessed directly when an appropriate level of disease appears on untreated check plants (16-19 days after application).

*Puccinia triticina* (also known as recondata, Brown rust on wheat). 2-week old wheat plants cv. Arina are sprayed in a spray chamber with the formulated test compound diluted in water. The test plants are inoculated by spraying them with a spore suspension one day after application. After an incubation period of 1 day at 20° C. and 95% rh, the inoculated test plants are kept at 20° C./18° C. (day/night) and 60% rh in a greenhouse. The percentage leaf area covered by disease is assessed when an appropriate level of disease appears on untreated check plants (12-14 days after application).

*Botrytis cinerea* tomato/preventative (*Botrytis* on tomato) 4-week old tomato plants cv. Roter Gnom are treated in a spray chamber with the formulated test compound diluted in water. The test plants are inoculated by spraying them with a spore suspension two days after application. The inoculated test plants are incubated at 20° C. and 95% rh in a greenhouse and the percentage leaf area covered by disease is assessed when an appropriate level of disease appears on untreated check plants (5-6 days after application).

*Mycosphaerella arachidis* peanut/preventative (Brown leaf spot on groundnut) 3-week old peanut plants cv. Georgia Green are sprayed in a spray chamber with the formulated test compound diluted in water. The test plants are inoculated by spraying them with a spore suspension on their lower leaf surface one day after application. After an incubation period of 4 days under a plastic hood at 23° C. and 100% rh, the inoculated test plants are kept at 23° C./20° C. (day/night) and 70% rh in a greenhouse. The percentage leaf area covered by disease is assessed when an appropriate level of disease appears on untreated check plants (12-14 days after application).

| Disease | crop | application timing | efficacy 40 g/ha (%) | efficacy 20 g/ha (%) |
|---|---|---|---|---|
| Zymoseptoria tritici | wheat | 1 day preventative | 16 | 44 |
| Puccinia triticina | wheat | 2 days preventative | 81 | 81 |
| Botrytis cinerea | tomato | 2 days preventative | 47 | 30 |
| Mycosphaerella arachidis | groundnut | 1 day preventative | 65 | 56 |

Results indicate a m is active as a fungicide to reduce disease seventy on plants in the greenhouse.

Example 7: The Effect of Tween 20 on the Efficacy of Purified CtmC on *Fusarium virguliforme*

Prior art WO2015191789 clearly states that the inventors found no fungal inhibitory action for Cyclothiazomycin C. This is contrary to our results. In order to eliminate the possibility that the fungicidal effect that we observe was down to the presence of Tween 20 we carried out some experiments like those in Example 3 but with various levels of Tween 20, including none.

The experiment at outlined in Example 3 was repeated to evaluate the EC50 values for CtmC control on *Fusarium virguliforme* in presence of 4 different rates of Tween20: 0% (absence of Tween 20), 0.0025%, 0.0050% (identical to Example 3) and 0.0100%. The plate layout was identical to Example 3, except that the plates were multiplied 4 times to accommodate the different Tween 20 concentrations in the assay plate. All other experimental conditions were kept identical. *Fusarium* isolates were tested at 25'000 sp/ml.

TABLE 3

EC50 calculation for 2 fungal isolates in presence of different concentrations of Tween20, in ppm. Values are an average over all replica treatments in the experiment.

| | Tween 20 | | | |
|---|---|---|---|---|
| CtmC; EC50 (ppm) | 0% | 0.0025% | 0.0050% | 0.0100% |
| *Fusarium virguliforme* isolate 1 | 1.422 | 1.053 | 0.8103 | 1.436 |
| *Fusarium virguliforme* isolate 2 | 1.098 | 0.889 | 0.7844 | 1.035 |

The results are consistent with Example 3 and indicate that Tween 20 has no significant influence on the EC50 value for *Fusarium virguliforme* control in-vitro.

Example 8: Efficacy of Purified CtmC on Further Extended List of Fungal Species In-Vitro CtmC was dissolved in DMSO (Dimethylsulfoxid) to a final concentration of 1000 ppm to create a stock solution. A second dilutions of 1:10 was made in water+0.025% Tween 20. From this second dilution 10 ul are dispensed into a 96 well plate. To each well, 90 ul of medium (PDB—potato dextrose broth, plus 0.3% agar) with fungal spores are added and mixed, resulting in final CtmC concentrations of 10 ppm. All wells containing CtmC also contain DMSO (1%) and Tween 20 (0.0025%). In the following table 4 some of the species were tested using several distinct isolates (internal strain number indicated) to understand variability among different isolates of the same species sampled in different locations, producing different mycotoxins (genus *Fusarium*), or expressing various tolerances to fungicides of the SDHI (Succinate Dehydrogenase Inhibitor), SBI (Sterol Biosynthesis Inhibitors) and/or QoI (quinone outside inhibitors) classes (example: *Zymoseptoria tritici*). Different isolates had variable inoculum density and number of biological replicas, as indicated.

TABLE 4

Disease control efficacy calculation for additional fungal isolates in presence of different concentrations of Tween20, in ppm. Values are an average overall replica treatments in the experiment.

| species | isolate | spore density (per ml) | reps | blank | untreated | CtmC 10 ppm (OD) | CtmC 10 ppm (efficacy %) |
|---|---|---|---|---|---|---|---|
| *Cercospora kikuchii* | K6080 | 25,000 | 4 | 0.044 | 0.215 | 0.043 | 100 |
| *Cercospora sojina* | K5703 | 25,000 | 4 | 0.047 | 0.357 | 0.188 | 54 |
| *Cochliobolus sativus* | K5817 | 30,000 | 4 | 0.044 | 0.701 | 0.095 | 92 |
| *Colletotrichum lindemuthianum* | K5893 | 25,000 | 4 | 0.046 | 0.373 | 0.225 | 45 |
| *Colletotrichum orbiculare* | K5770 | 25,000 | 8 | 0.035 | 0.449 | 0.218 | 56 |
| *Corynespora cassiicola* | K5577 | 25,000 | 4 | 0.047 | 0.427 | 0.100 | 86 |
| *Fusarium avenaceum* | K6940 | 25,000 | 3 | 0.054 | 0.410 | 0.225 | 52 |
| *Fusarium culmorum* | K5488 | 25,000 | 4 | 0.046 | 0.374 | 0.203 | 52 |
| *Fusarium culmorum* | K6937 | 15,000 | 3 | 0.052 | 0.528 | 0.319 | 44 |
| *Fusarium culmorum* | K8196 | 15,000 | 3 | 0.055 | 0.701 | 0.388 | 48 |
| *Fusarium langsethiae* | K5670 | 25,000 | 3 | 0.053 | 0.346 | 0.072 | 94 |
| *Fusarium poae* | K8039 | 25,000 | 3 | 0.050 | 0.619 | 0.267 | 62 |
| *Fusarium sporotrichioides* | K7901 | 25,000 | 3 | 0.052 | 0.666 | 0.231 | 71 |
| *Fusarium tricinctum* | K7452 | 25,000 | 3 | 0.052 | 0.498 | 0.197 | 68 |
| *Fusarium tricinctum* | K7454 | 20,000 | 4 | 0.050 | 0.463 | 0.195 | 65 |
| *Gibberella avenacea* | K6939 | 25,000 | 4 | 0.055 | 0.675 | 0.165 | 82 |
| *Gibberella fujikuroi* | K5299 | 25,000 | 3 | 0.053 | 0.941 | 0.528 | 47 |
| *Gibberella zeae* | K6102 | 25,000 | 4 | 0.044 | 0.733 | 0.377 | 52 |
| *Gibberella zeae* | K6934 | 25,000 | 3 | 0.052 | 0.641 | 0.361 | 48 |
| *Microdochium majus* | K7482 | 25,000 | 3 | 0.050 | 0.228 | 0.057 | 96 |
| *Monographella nivalis* | K7484 | 25,000 | 3 | 0.054 | 0.233 | 0.073 | 90 |
| *Pyrenophora tritici-repentis* | K6186 | mycelium | 4 | 0.046 | 0.508 | 0.094 | 90 |
| *Ramularia collo-cygni* | K6218 | 60,000 | 4 | 0.043 | 0.231 | 0.119 | 60 |
| *Rhynchosporium secalis* | K5917 | 180,000 | 4 | 0.046 | 0.378 | 0.062 | 95 |
| *Septoria glycines* | K5204 | 25,000 | 4 | 0.044 | 0.414 | 0.115 | 81 |
| *Tilletia tritici* | K5212 | 30,000 | 4 | 0.046 | 0.451 | 0.062 | 96 |
| *Ustilago segetum var. tritici* | K5349 | 30,000 | 4 | 0.044 | 0.304 | 0.051 | 97 |
| *Venturia inaequalis* | K6222 | 120,000 | 4 | 0.044 | 0.320 | 0.082 | 86 |
| *Zymoseptoria tritici* | K6105 | 100,000 | 20 | 0.044 | 0.354 | 0.046 | 99 |
| *Zymoseptoria tritici* | K6318 | 100,000 | 4 | 0.054 | 0.253 | 0.059 | 98 |
| *Zymoseptoria tritici* | K6420 | 100,000 | 4 | 0.048 | 0.257 | 0.064 | 93 |
| *Zymoseptoria tritici* | K7953 | 100,000 | 4 | 0.055 | 0.235 | 0.096 | 77 |

The results indicate a large variety of fungal species can at least partially be controlled, and that several isolates of the same species have comparable sensitivity to CtmC.

The invention claimed is:

1. A method of controlling or preventing infestation of plants by a fungi, comprising applying a fungicidally effective amount of cyclothiazomycin C to the plants, to parts thereof or the locus thereof.

2. The method of claim 1, wherein the plants are cereals, groundnut or soybean plants.

3. The method claim 1, wherein the plants are wheat.

4. The method of claim 1, wherein the fungi are selected from the group consisting of: *Botrytis cinerea, Cercospora kikuchii, Cercospora sojina, Cochlobolus sativus, Colletotrichum lindemuthianum, Colletotrichum orbiculare, Corynespora cassiicola, Fusarium avenaceum, Fusarium culmorum, Fusarium langsethiae, Fusarium poae, Fusarium sporotrichioides, Fusarium tricinctum, Fusarium virguliforme, Gibberella avenacea, Gibberella fujikuroi, Gibberella zeae, Microdochium majus, Monographella nivalis, Mycosphaerella arachidis, Phakopsora pachyrhizi, Puccinia triticina, Pyrenophora tritici-repentis, Ramularia collo cygni, Rhynchosporium secalis, Septoria glycines, Tilletia tritici, Ustilago segetum* var. *Tritici, Venturia inaequalis*, and *Zymoseptoria tritici*.

5. The method of claim 1, wherein the fungi are selected from the group consisting of *Botrytis cinerea, Fusarium virguliforme, Monographella nivalis, Mycosphaerella arachidis, Phakopsora pachyrhizi, Puccinia triticina* or *Zymoseptoria tritici*.

6. The method of claim 1 wherein the applying of the cyclothiazomycin C is to the plants at a rate of 5 g to 6 kg per hectare.

7. The method of claim 1, wherein the applying is to the plant.

8. The method of claim 7, wherein the applying of the cyclothiazomycin C is at a rate of 10 g to 1 kg per hectare.

9. The method of claim 7, wherein the applying of the cyclothiazomycin C is at a rate of 20 g to 600 g per hectare.

10. The method of claim 7, wherein the plant is wheat.

11. The method of claim 7, wherein the plant is soybean.

12. The method of claim 7, wherein the plant is groundnut.

13. The method of claim 7, wherein the fungi are selected from the group consisting of: *Botrytis cinerea, Fusarium virguliforme, Monographella nivalis, Mycosphaerella arachidis, Phakopsora pachyrhizi, Puccinia triticina* and *Zymoseptoria tritici*.

14. The method of claim 1, wherein the applying is to parts thereof.

15. The method of claim 14, wherein the parts thereof is a seed.

16. The method of claim 14, wherein the fungi are selected from the group consisting of: *Botrytis cinerea, Fusarium virguliforme, Monographella nivalis, Mycosphaerella arachidis, Phakopsora pachyrhizi, Puccinia triticina* and *Zymoseptoria tritici*.

17. The method of claim 14, wherein the applying of the cyclothiazomycin C is at a rate of 0.01 to 10 g per kg of seed.

18. The method of claim 1, wherein the applying is to the locus thereof.

* * * * *